(12) United States Patent
Muthusamy et al.

(10) Patent No.: US 12,091,388 B2
(45) Date of Patent: Sep. 17, 2024

(54) SOLID STATE FORMS OF REPROXALAP

(71) Applicant: TEVA PHARMACEUTICALS INTERNATIONAL GMBH, Jona (CH)

(72) Inventors: Anantha Rajmohan Muthusamy, Sivakasi (IN); Sundara Lakshmi Kanniah, Vellore (IN); Rahul Kumar Reddy Putikum, Mahabubnagar (IN); Sudhanshu Saxena, Mumbai (IN); Amol Bandal, Raigad District (IN)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 700 days.

(21) Appl. No.: 17/311,746

(22) PCT Filed: Dec. 12, 2019

(86) PCT No.: PCT/US2019/065836
§ 371 (c)(1),
(2) Date: Jun. 8, 2021

(87) PCT Pub. No.: WO2020/123730
PCT Pub. Date: Jun. 18, 2020

(65) Prior Publication Data
US 2022/0009893 A1    Jan. 13, 2022

(30) Foreign Application Priority Data

Dec. 12, 2018 (IN) .............................. 201811047061
Feb. 22, 2019 (IN) .............................. 201911007092

(51) Int. Cl.
*C07D 215/38* (2006.01)

(52) U.S. Cl.
CPC ........ *C07D 215/38* (2013.01); *C07B 2200/13* (2013.01)

(58) Field of Classification Search
CPC ................................................. C07D 215/38
See application file for complete search history.

(56) References Cited

U.S. PATENT DOCUMENTS

| 2018/0050989 A1 | 2/2018 | Machatha et al. |
| 2018/0265474 A1 | 9/2018 | Buist et al. |

OTHER PUBLICATIONS

Mino R. Caira. "Crystalline Polymorphism of Organic Compounds", Topics in Current Chemistry, vol. 198, pp. 163-208 (1998).
International Search Report and Written Opinion of the International Searching Authority issued in corresponding application PCT/US2019/065836 mailed Mar. 11, 2020 (16 pages).

*Primary Examiner* — Samantha L Shterengarts
*Assistant Examiner* — Karen Cheng
(74) *Attorney, Agent, or Firm* — Carter, DeLuca & Farrell LLP (57) ABSTRACT

The present disclosure relates to solid state forms of Reproxalap salts, processes for the preparation thereof, pharmaceutical formulations/compositions thereof, and methods of use thereof.

11 Claims, 4 Drawing Sheets

Figure 1: An X-ray powder diffraction pattern (XRPD) of Form R1 of Reproxalap borate.

Figure 2: An X-ray powder diffraction pattern (XRPD) of Form S1 of Reproxalap 1,5-naphthalenedisulfonate Figure 3: An X-ray powder diffraction pattern (XRPD) of Form U1 of Reproxalap 1, 2- ethanedisulfonate Figure 4: An X-ray powder diffraction pattern (XRPD) of Form P1 of Reproxalap methanesulfonate

SOLID STATE FORMS OF REPROXALAP

CROSS REFERENCE TO RELATED APPLICATIONS

This application is a National Stage of, and claims priority to and the benefit of, International Patent Application No. PCT/US2019/065836 filed Dec. 12, 2019, which, in turn, claims the benefit of and priority to, Indian Provisional Application No. 201811047061 filed Dec. 12, 2018 and Indian Provisional Application No. 201911007092 filed Feb. 22, 2019, the entire disclosures of each of which are incorporated by reference herein.

TECHNICAL FIELD

The present disclosure relates to solid state forms of Reproxalap salts, processes for the preparation thereof, pharmaceutical formulations/compositions thereof, and methods of use thereof.

BACKGROUND

Reproxalap chemical name is 2-(3-amino-6-chloroquinolin-2-yl)propan-2-ol, having the following chemical structure:

Reproxalap is a small molecule RASP (Reactive Aldehyde Species) inhibitor under development for the treatment of dry eye disease, allergic conjunctivitis, noninfectious anterior uveitis, and Sjögren-Larsson Syndrome.

U.S. Pat. No. 7,973,025 (referred to herein as '025) discloses Reproxalap. U.S. Patent Application Publication Number 2013/0190500 (referred to herein as '500) discloses a process for preparation of Reproxalap. U.S. Patent Application Publication Number 2018/0265474 (referred to herein as '474) discloses mesylate, besylate, sulfate, tosylate, hydrochloride, oxalate, phosphate, camsylate and tartrate salts and polymorphs of Reproxalap.

Polymorphism, the occurrence of different crystal forms, is a property of some molecules and molecular complexes. A single compound, like Reproxalap or a salt thereof, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state (13C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorphic as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts and solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional solid state forms (including solvated forms) of Reproxalap salts.

SUMMARY OF THE DISCLOSURE

The present disclosure relates to crystalline forms of Reproxalap borate, Reproxalap 1,5-naphthalenedisulfonate, Reproxalap 1,2-ethanedisulfonate and/or Reproxalap methanesulfonate (may also referred to as Reproxalap mesylate).

The present disclosure also relates to the uses of solid state forms of Reproxalap salts of the present disclosure, for preparing other salts and their solid state forms, as well as solid state forms of Reproxalap.

The present disclosure also encompasses the uses of the above described solid state forms of Reproxalap salts for the preparation of pharmaceutical compositions and/or formulations.

In another embodiment, the present disclosure encompasses pharmaceutical compositions comprising the any one or a combination of the above described solid state forms of Reproxalap salts.

In yet another embodiment, the present disclosure encompasses pharmaceutical formulations comprising any one or a combination of the above described solid state forms of Reproxalap salts, and at least one pharmaceutically acceptable excipient. The pharmaceutical formulations may be in the form of ophthalmic solution or a topical cream and/or an ointment.

The present disclosure further encompasses processes to prepare said pharmaceutical formulations of solid state forms of Reproxalap salts comprising combining any one or a combination of the above described solid state forms of Reproxalap salts, or pharmaceutical compositions comprising them, and at least one pharmaceutically acceptable excipient.

The solid state forms of Reproxalap salts defined herein as well as the pharmaceutical compositions and formulations of the solid state form of the Reproxalap salts can be used as medicaments, particularly for the treatment of dry eye disease, allergic conjunctivitis, noninfectious anterior uveitis, and Sjögren-Larsson Syndrome, comprising administering a therapeutically effective amount of any one or a combination of the solid state form of Reproxalap salts of the present disclosure, or at least one of the above pharmaceutical compositions or formulations, to a subject which needs the treatment of dry eye disease, allergic conjunctivitis, noninfectious anterior uveitis, and/or Sjögren-Larsson Syndrome, or otherwise in need of the treatment. The pharmaceutical formulations may be in the form of ophthalmic solution or a topical cream and/or an ointment. In embodiments, the ophthalmic solution is used for the treatment of dry eye disease, allergic conjunctivitis, noninfectious anterior uveitis, and/or Sjögren-Larsson Syndrome. In other embodiments, the topical cream and/or an ointment is used for the treatment of Sjögren-Larsson Syndrome.

The present disclosure also provides the uses of the solid state forms of Reproxalap salts of the present disclosure, or at least one of the above pharmaceutical compositions or formulations, for the manufacture of medicaments for the treatment of dry eye disease, allergic conjunctivitis, noninfectious anterior uveitis, and/or Sjögren-Larsson Syndrome.

In another aspect, the present disclosure encompasses the above solid state forms of Reproxalap salts for use in medicine, preferably for the treatment of dry eye disease, allergic conjunctivitis, noninfectious anterior uveitis, and/or Sjögren-Larsson Syndrome.

DETAILED DESCRIPTION OF THE DISCLOSURE

The present disclosure relates to solid state forms of Reproxalap salts, to processes for preparation thereof and to pharmaceutical compositions and formulations comprising these solid state forms and/or combinations thereof. Particularly, the present disclosure relates to solid state forms of Reproxalap borate, Reproxalap 1,5-naphthalenedisulfonate, Reproxalap 1,2-ethanedisulfonate and Reproxalap methanesulfonate.

The solid state forms of Reproxalap salts according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form of Reproxalap salt, referred to herein as being characterized by graphical data "as depicted in" a Figure will thus be understood to include any crystal form of the Reproxalap salt, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD.

Thus, solid state form of Reproxalap salt described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject solid state form of Reproxalap salt.

In some embodiments of the disclosure, the described solid state forms of Reproxalap salt may contain from about 1% to about 20% (w/w), from about 5% to about 20% (w/w), or from about 5% to about 10% (w/w) of one or more other solid state forms of Reproxalap salt.

As used herein, unless stated otherwise, XRPD peaks reported herein are preferably measured using CuKα radiation, λ=1.5418 Å, preferably, XRPD peaks reported herein are measured using CuK α radiation, λ=1.5418 Å, at a temperature of 25±3° C.

As used herein, the term "isolated" in reference to the solid state forms of Reproxalap salts of the present disclosure corresponds to solid state form of Reproxalap salt that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

As used herein, and unless stated otherwise, the term "anhydrous" in relation to a crystalline Reproxalap salt relates to a crystalline Reproxalap salt which does not include any crystalline water (or other solvents) in a defined, stoichiometric amount within the crystal. Moreover, an "anhydrous" form does not contain more than about 1% (w/w) of either water or organic solvents as measured for example by TGA or by KF.

As used herein, the term "isolated" in reference to crystalline polymorph of Reproxalap of the present disclosure corresponds to a crystalline polymorph of Reproxalap that is physically separated from the reaction mixture in which it is formed.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding (methyl tert-butyl ether) MTBE (1.5 v/v) to a 100 ml reaction mixture would indicate that 150 mL of MTBE was added.

As used herein the term non-hygroscopic in relation to a crystalline form of Reproxalap salt, refers to less than about 1.0% (w/w) absorption of water at about 25° C. and about 80% relative humidity (RH), by the crystalline form of Reproxalap salt as determined for example by TGA.

As used herein and unless indicated otherwise, the term "ambient conditions" refer to atmospheric pressure and a temperature of 22-24° C.

As used herein, the term "reduced pressure" refers to a pressure of about 10 mbar to about 500 mbar.

The present disclosure comprises Reproxalap borate.

Figure 1:
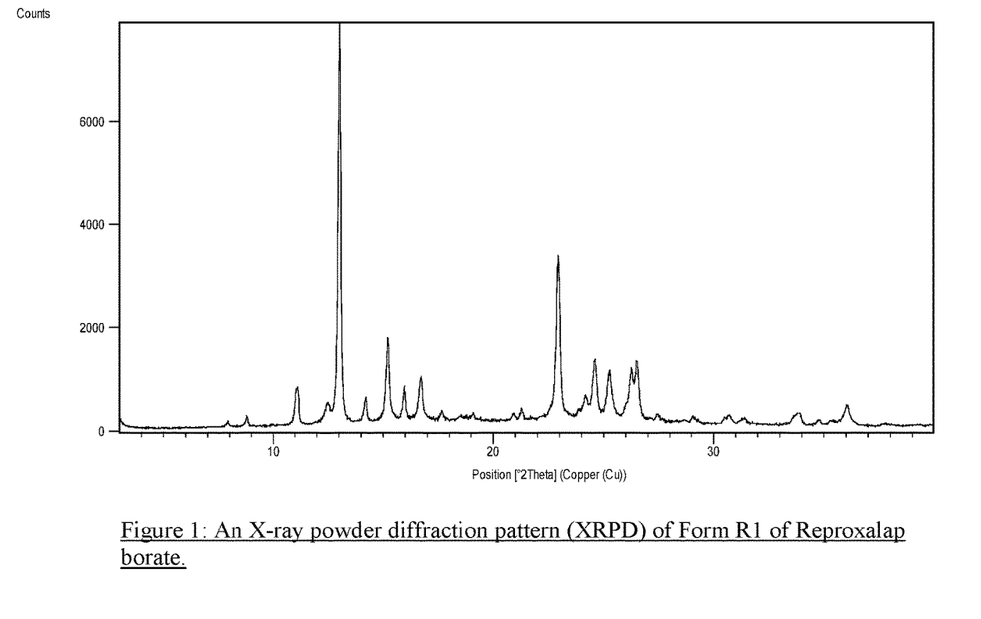
FIG. 1 shows a characteristic X-ray powder diffraction pattern (XRPD) of Form R1 of Reproxalap borate.

The present disclosure further comprises a crystalline polymorph of Reproxalap borate, designated as Form R1. The crystalline Form R1 of Reproxalap borate may be characterized by data selected from one or more of the following: an X-ray powder diffraction pattern substantially as depicted in FIG. 1; an X-ray powder diffraction pattern having peaks at 13.1, 15.3, 16.0, 16.8 and 23.0 degrees 2-theta±0.2 degrees 2-theta; and combinations of these data.

Crystalline Form R1 of Reproxalap borate may be further characterized by an X-ray powder diffraction pattern having peaks at 13.1, 15.3, 16.0, 16.8 and 23.0 degrees 2-theta±0.2 degrees 2-theta, and also having any one, two, three, four or five additional peaks selected from the group consisting of at 11.2, 14.2, 24.2, 24.7 and 25.3 degrees 2-theta±0.2 degrees 2-theta.

In embodiments, crystalline Form R1 of Reproxalap borate may be characterized by an X-ray powder diffraction pattern having peaks at: 11.2, 13.1, 14.2, 15.3, 16.0, 16.8, 23.0, 24.2, 24.7, 25.3 degrees 2-theta±0.2 degrees 2-theta.

In one embodiment of the present disclosure, Crystalline Form R1 of Reproxalap borate is a hydrate. Typically, the water content in Crystalline Form R1 of Reproxalap borate is from about 3% to about 7% (w/w), as measured by TGA.

Crystalline Form R1 of Reproxalap borate may be characterized by each of the above characteristics alone/or by all possible combinations, e.g., an XRPD pattern having peaks at 13.1, 15.3, 16.0, 16.8 and 23.0 degrees 2-theta±0.2 degrees 2-theta; an XRPD pattern as depicted in FIG. 1, and combinations thereof.

In one embodiment of the present disclosure, Form R1 of Reproxalap borate is isolated.

The step of isolating Reproxalap borate or crystalline polymorph of Reproxalap borate may be performed by crystallization.

In embodiments, the present disclosure provides a process for preparing Reproxalap borate, typically crystalline form R1 of Reproxalap borate, comprising precipitating Reproxalap borate from methanol. In an embodiment, the process for preparing Reproxalap borate comprises combining a solution of Reproxalap with boric acid. The Reproxalap may be in a solution with a suitable solvent. The solvent may be a polar solvent, such as an alcohol, e.g. a $C_{1-6}$ alcohol. In embodiments, methanol, ethanol and propanol may be used. In a particular embodiment, a process for preparing Reproxalap borate comprises combining a solution of Reproxalap in methanol with boric acid, for example by adding boric acid to a solution of Reproxalap in methanol or by adding a solution of Reproxalap to boric acid.

In specific embodiments, the process comprises adding boric acid to a solution of Reproxalap in methanol. In another embodiment Reproxalap borate form R1 precipitates.

In any embodiment of the process for preparing Reproxalap borate as defined in any embodiment herein, boric acid may be added to a solution of Reproxalap in the solvent. In any embodiment of the process, the combining of Reproxalap solution and boric acid may be carried out at a temperature of about 15° C. to about 50° C., about 20° C. to about 40° C. or about 20° C. to about 30° C. The quantity of solvent in the Reproxalap solution may be about 5 ml to about 40 ml per gram of Reproxalap, or about 10 ml to about 35 ml per gram of Reproxalap, or about 20 ml to about 30 ml per gram of Reproxalap, or about 25 ml per gram of Reproxalap. In any embodiment of the process, the mixture obtained after combining the boric acid and Reproxalap solution may be heated, optionally to a temperature of about 30° C. to about 65° C., about 40° C. to about 60° C., about 45° C. to about 55° C. or about 50° C. The heating may be carried out for about 5 minutes to about 80 minutes, about 15 minutes to about 60 minutes, about 15 minutes to about 40 minutes, or about 30 minutes. After heating, the mixture may be cooled, typically to a temperature of about 5° C. to about 40° C., about 10° C. to about 40° C. or about 20° C. to about 30° C. The cooling may be carried out over a period of about 15 minutes to about 180 minutes, about 30 minutes to about 120 minutes, about 30 minutes to about 80 minutes, about 40 to about 70 minutes, or about 60 minutes. The mixture may be further maintained at a temperature of about 5° C. to about 40° C., about 10° C. to about 40° C. or about 20° C. to about 30° C., in embodiments for about 1 hour to about 24 hours, about 4 hours to about 15 hours, about 6 hours to about 10 hours or about 8 hours.

Reproxalap borate, typically Reproxalap borate Form R1 may be isolated from the mixture by any suitable method, such as by filtration. Prior to isolating the Reproxalap borate, the mixture can be cooled to a temperature of about 0° C. to about 20° C., about 2° C. to about 10° C. or about 2° C. to about 8° C., or about 5° C., typically over a time period of about 5 minutes to about 60 minutes, about 15 minutes to about 45 minutes, about 20 minutes to about 40 minutes, or about 30 minutes. Optionally the mixture may be held at this temperature for about 15 minutes to about 300 minutes, about 30 minutes to about 240 minutes, about 60 minutes to about 150 minutes, or about 120 minutes prior to isolating the Reproxalap borate.

The process may further include isolating the obtained polymorph R1 of Reproxalap borate, for example by filtration. Following isolation, the Reproxalap borate may be dried. The drying may be carried out during e.g. filtration. Optionally or additionally, the Reproxalap borate may be dried under reduced pressure (such as in a vacuum tray dryer), typically at a temperature of about 25° C. to about 80° C., about 30° C. to about 75° C., about 40° C. to about 70° C., about 55° C. to about 65° C., or about 60° C. The drying may be carried out for any suitable time to remove the solvent, typically about 1 to about 14 hours, about 4 to about 12 hours, about 6 to about 10 hours, or about 8 hours.

In some embodiments, the isolated Reproxalap borate, which may be form R1 of Reproxalap borate is dried under vacuum at a temperature of about 60° C., typically for a period of about 8 hours.

The process for preparing Reproxalap borate according to any embodiment described herein, may further comprise combining the product with at least one pharmaceutically acceptable excipient to form a pharmaceutical composition or a pharmaceutical formulation (typically an ophthalmic solution or a topical cream and/or ointment). Alternatively, the Reproxalap borate may be converted to another solid state form thereof, or another Reproxalap salt, or Reproxalap, prior to combining with a pharmaceutically acceptable excipient.

The present disclosure comprises a crystalline polymorph of Reproxalap 1,5-naphthalenedisulfonate, designated as Form S1. The crystalline Form S1 of Reproxalap 1,5-naphthalenedisulfonate may be characterized by data selected from one or more of the following: an X-ray powder diffraction pattern substantially as depicted in FIG. 2; an X-ray powder diffraction pattern having peaks at 10.6, 14.4, 16.7, 21.9 and 23.6 degrees 2-theta±0.2 degrees 2-theta; and combinations of these data.

Crystalline Form S1 of Reproxalap 1,5-naphthalenedisulfonate may be further characterized by an X-ray powder diffraction pattern having peaks at 10.6, 14.4, 16.7, 21.9 and 23.6 degrees 2-theta±0.2 degrees 2-theta, and also having any one, two, three, four or five additional peaks selected from the group consisting of at 13.7, 19.8, 25.6 and 29.0 degrees 2-theta±0.2 degrees 2-theta.

In one embodiment of the present disclosure, Crystalline Form S1 of Reproxalap 1,5-naphthalenedisulfonate is an anhydrous form.

Figure 2:
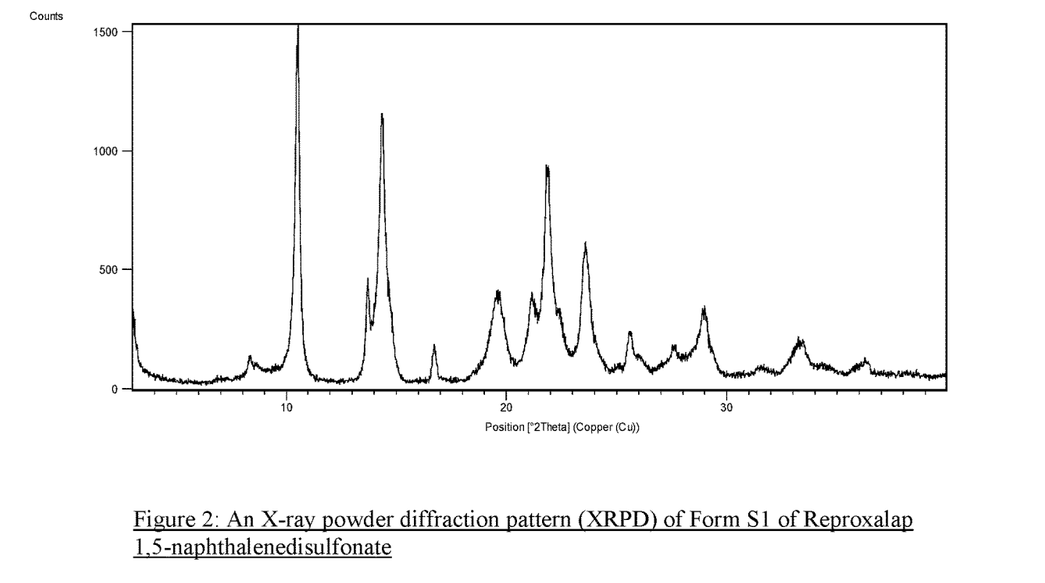
FIG. 2 shows a characteristic X-ray powder diffraction pattern (XRPD) of Form S1 of Reproxalap 1,5-naphthalenedisulfonate.

Crystalline Form S1 of Reproxalap 1,5-naphthalenedisulfonate may be characterized by each of the above characteristics alone/or by all possible combinations, e.g., an XRPD pattern having peaks at 10.6, 14.4, 16.7, 21.9 and 23.6 degrees 2-theta±0.2 degrees 2-theta; an XRPD pattern as depicted in FIG. 2, and combinations thereof.

In one embodiment of the present disclosure, Form S1 of Reproxalap 1,5-naphthalenedisulfonate is isolated.

The step of isolating Reproxalap 1,5-naphthalenedisulfonate or crystalline polymorph of Reproxalap 1,5-naphthalenedisulfonate may be performed by crystallization.

The present disclosure comprises a crystalline polymorph of Reproxalap 1,2-ethanedisulfonate, designated as Form U1. The crystalline Form U1 of Reproxalap 1,2-ethanedisulfonate may be characterized by data selected from one or more of the following: an X-ray powder diffraction pattern substantially as depicted in FIG. 3; an X-ray powder diffraction pattern having peaks at 5.1, 10.1, 11.4, 15.4 and 18.4 degrees 2-theta±0.2 degrees 2-theta; and combinations of these data.

Crystalline Form U1 of Reproxalap 1,2-ethanedisulfonate may be further characterized by an X-ray powder diffraction pattern having peaks at 5.1, 10.1, 11.4, 15.4 and 18.4 degrees 2-theta±0.2 degrees 2-theta, and also having any one, two, three, four or five additional peaks selected from the group consisting of at 12.4, 13.4, 19.1, 22.3 and 27.1 degrees 2-theta±0.2 degrees 2-theta.

In one embodiment of the present disclosure, Crystalline Form U1 of Reproxalap 1,2-ethanedisulfonate is an anhydrous form.

Figure 3:
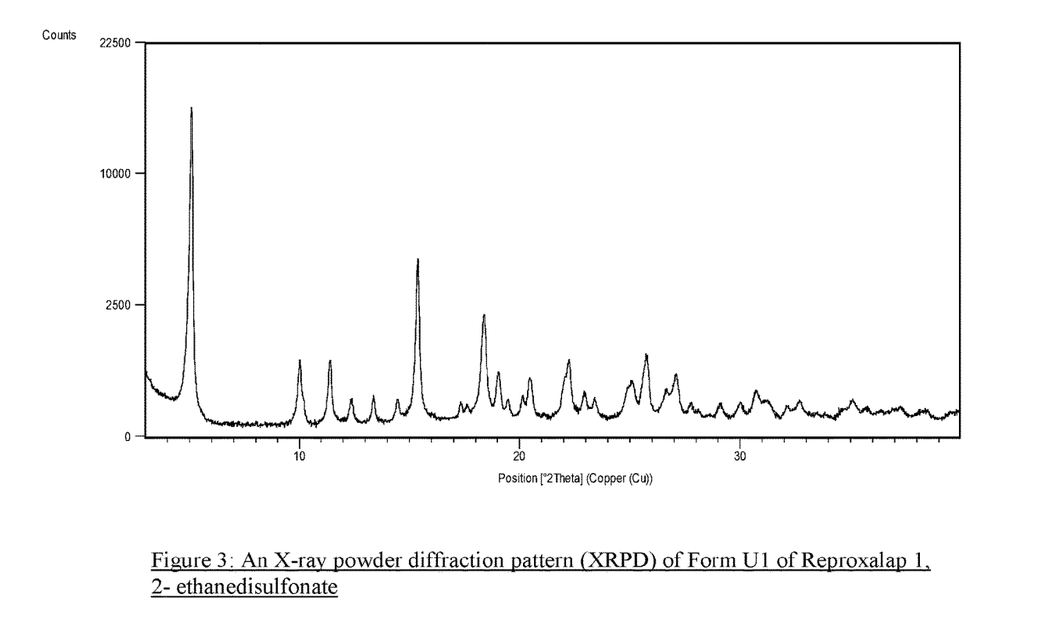
FIG. 3 shows a characteristic X-ray powder diffraction pattern (XRPD) of Form U1 of Reproxalap 1,2-ethanedisulfonate.

Crystalline Form U1 of Reproxalap 1,2-ethanedisulfonate may be characterized by each of the above characteristics alone/or by all possible combinations, e.g., an XRPD pattern having peaks at 5.1, 10.1, 11.4, 15.4 and 18.4 degrees 2-theta±0.2 degrees 2-theta; an XRPD pattern as depicted in FIG. 3, and combinations thereof.

In one embodiment of the present disclosure, Form U1 of Reproxalap 1,2-ethanedisulfonate is isolated.

The step of isolating Reproxalap 1,2-ethanedisulfonate or crystalline polymorph of Reproxalap 1,2-ethanedisulfonate may be performed by crystallization.

The present disclosure comprises a crystalline polymorph of Reproxalap methanesulfonate, designated as Form P1. The crystalline Form P1 of Reproxalap methanesulfonate may be characterized by data selected from one or more of the following: an X-ray powder diffraction pattern substantially as depicted in FIG. 4; an X-ray powder diffraction pattern having peaks at 8.2, 13.4, 17.7, 18.1, 20.6 and 25.9 degrees 2-theta±0.2 degrees 2-theta; and combinations of these data.

Crystalline Form P1 of Reproxalap methanesulfonate may be further characterized by an X-ray powder diffraction pattern having peaks at 8.2, 13.4, 17.7, 18.1, 20.6 and 25.9 degrees 2-theta±0.2 degrees 2-theta, and also having any one, two, three, four or five additional peaks selected from the group consisting of at 11.0, 15.3, 22.5, 23.2 and 29.3 degrees 2-theta±0.2 degrees 2-theta.

In embodiments, crystalline Form P1 of Reproxalap Methanesulfonate may be characterized by an XRPD pattern having peaks at: 8.2, 11.0, 13.4, 15.3, 17.7, 18.1, 20.6, 22.5, 23.2, 25.9, 29.3 degrees 2-theta±0.2 degrees 2-theta. In one embodiment of the present disclosure, Crystalline form P1 of Reproxalap methanesulfonate is a hydrate. Typically, the water content in Crystalline Form P1 of Reproxalap methanesulfonate is from about 3% to about 6% (w/w), preferably about 4% as measured by TGA.

Figure 4:
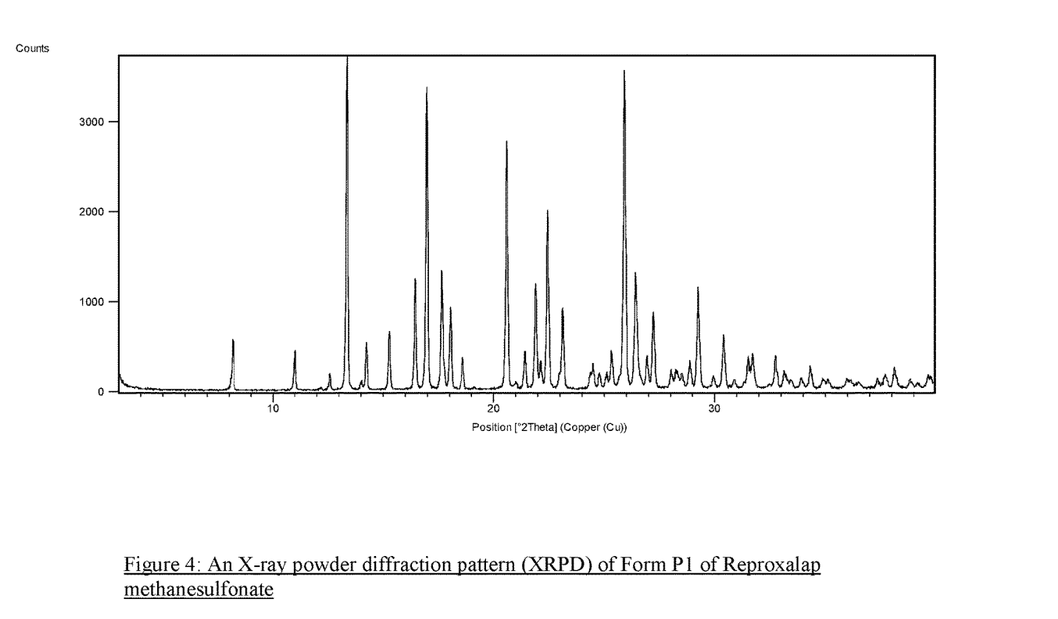
FIG. 4 shows a characteristic X-ray powder diffraction pattern (XRPD) of Form P1 of Reproxalap methanesulfonate.

Crystalline Form P1 of Reproxalap methanesulfonate may be characterized by each of the above characteristics alone/or by all possible combinations, e.g., an XRPD pattern having peaks at 8.2, 13.4, 17.7, 18.1, 20.6 and 25.9 degrees 2-theta±0.2 degrees 2-theta; an XRPD pattern as depicted in FIG. 4, and combinations thereof.

In one embodiment of the present disclosure, Form P1 of Reproxalap methanesulfonate is isolated.

The step of isolating Reproxalap methanesulfonate or crystalline polymorph of Reproxalap methanesulfonate may be performed by crystallization.

In specific embodiment, the present disclosure provides a process for preparing form P1 of Reproxalap methanesulfonate comprising precipitating Reproxalap methanesulfonate form P1 from a mixture comprising ethanol, tetrahydrofuran ("THF") and methyl tert-butyl ether ("MTBE"). In embodiments, the present disclosure provides a process for preparing form P1 of Reproxalap methanesulfonate comprising combining a solution of Reproxalap in ethanol, a solution of methanesulfonic acid in THF and MTBE to precipitate Reproxalap methanesulfonate salt. In embodiments, the process includes the following steps:

i) combining a solution of methane sulfonic acid in THF with a solution of Reproxalap in ethanol; and
ii) adding MTBE to precipitate Reproxalap methanesulfonate form P1.

In any embodiment of the process, the solution of Reproxalap in ethanol is prepared by dissolution of Reproxalap in ethanol, typically at a temperature of about 15° C. to about 50° C., about 18° C. to about 35° C., or about 20° C. to about 30° C. The solution may be optionally heated prior to combining with methane sulfonic acid in THF, typically to a temperature of from about about 30° C. to about 70° C., about 40° C. to about 60° C., or about 50° C. In any embodiment of this process, the ethanol in step (i) is typically used in an amount of about 2 ml to about 20 ml, about 5 ml to about 15 ml, about 7 ml to about 12 ml, or about 10 ml, per gram of Reproxalap.

In any embodiment of this process, the combining of the solution of methane sulfonic acid in THF with the solution of Reproxalap in ethanol in step (i) may be carried out at a temperature of 20° C. to about 70° C., about 30° C. to about 65° C. or about 40° C. to about 60° C., or about 50° C. In any embodiment of the process, the THF is typically used in an amount of about 0.5 ml to about 20 ml, about 2 ml to about 10 ml, about 3 ml to about 5 ml, or about 4 to about 4.5 ml per gram of Reproxalap. Typically step (i) comprises adding the solution of methanesulfonic acid in THF to the solution of Reproxalap in ethanol. In any embodiment of the process, following the combination of the solution of methanesulfonic acid in THF to the solution of Reproxalap in ethanol, the mixture may be optionally maintained, typically at the same temperature, for about 5 minutes to about 40 minutes, about 10 minutes to about 20 minutes or about 10 minutes to about 15 minutes. In any embodiment of the process, following the combination of the solution of methanesulfonic acid in THF to the solution of Reproxalap in ethanol, the mixture may be optionally cooled, typically to a temperature of about 0° C. to about 30° C., about 0° C. to about 20° C., about 2° C. to about 20° C. or about 2° C. to about 10° C., or about 5° C., typically over a period of about 10 minutes to about 24 hours, about 20 minutes to about 20 hours, or about 30 minutes to about 10 hours.

In any embodiment of the process, the MTBE in step (ii) is typically used in an amount that is sufficient to precipitate the Reproxalap Methanesulfonate. In any embodiment of the process, MTBE is used in an amount of about 10 ml to about 150 ml, about 20 ml to about 120 ml, about 40 ml to about 100 ml, or about 50 to about 80 ml or about 60 to about 75 ml of MTBE, per gram of Reproxalap. In any embodiment of the process, the MTBE in step (ii) is typically added at a temperature of about 0° C. to about 50° C., about 0° C. to about 40° C., or about 5° C. to about 30° C. The mixture in step (ii) may be maintained at a temperature of about 0° C. to about 50° C., about 0° C. to about 40° C., about 5° C. to about 30° C., optionally with stirring. The mixture may be maintained at this temperature range, for about 1 hour to about 18 hours, about 1 hour to about 16 hours, about 2 hours to about 5 hours.

The process may further include isolating the obtain polymorph P1 of Reproxalap methanesulfonate, for example by filtration. In any embodiment of the process, the filtration may be carried out at a temperature of about 5° C. to about 40° C., about 10° C. to about 30° C. or about 15° C. to about 30° C., or about 20° C. to about 30° C. In any embodiment of the process, the isolated form P1 of Reproxalap methanesulfonate may be dried, preferably under vacuum. Such drying may be done at a temperature of from about 20° C. to about 70° C., about 25° C. to about 60° C., or about 30° C. to about 40° C., typically for a period of from about 4 hours to about 20 hours, about 8 hours to about 18 hours, about 12 to about 15 hours.

The obtained Reproxalap methanesulfonate form P1 may then be filtered and isolated. It may be washed preferably with MTBE, or alternatively it may directly dried, preferably as described herein above.

The process for preparing Reproxalap methanesulfonate according to any embodiment described herein, may further comprise combining the product with at least one pharmaceutically acceptable excipient to form a pharmaceutical composition or a pharmaceutical formulation (typically an ophthalmic solution or a topical cream and/or ointment). Alternatively, the Reproxalap methanesulfonate may be converted to another solid state form thereof, or another Reproxalap salt, or Reproxalap, prior to combining with a pharmaceutically acceptable excipient.

The above crystalline polymorphs of Reproxalap salts can be used to prepare other crystalline polymorphs of Reproxalap, other Reproxalap salts and their solid state forms thereof.

The present disclosure provides crystalline polymorphs of Reproxalap salts for use in the preparation of pharmaceutical compositions comprising Reproxalap or Reproxalap salts and/or crystalline polymorphs thereof.

The present disclosure also encompasses the use of crystalline polymorphs of Reproxalap salts of the present disclosure for the preparation of pharmaceutical compositions of crystalline polymorphs Reproxalap or Reproxalap salts and/or crystalline polymorphs thereof.

The present disclosure comprises processes for preparing the above mentioned pharmaceutical compositions. The processes comprise combining any one or a combination of the crystalline polymorphs of Reproxalap salts of the present disclosure with at least one pharmaceutically acceptable excipient.

Pharmaceutical formulations of the present invention contain any one or a combination of the solid state forms of Reproxalap salts of the present invention. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Reproxalap salt and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of Reproxalap salt can be administered. Reproxalap is preferably formulated for administration to a mammal, preferably a human, by injection. Reproxalap salt can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

Dosage forms for topical or transdermal administration of a pharmaceutical formulation of Reproxalap salt of the present disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Particularly, ophthalmic formulation, ear drops, and/or eye drops of Reproxalap salt of the present disclosure can be administered. Additionally, transdermal patches with Reproxalap salt of the present disclosure can be prepared. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

A pharmaceutical formulation of Reproxalap salt can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, Trans Ophthalmol Soc U K 104(Pt 4): 402-9; Ashton et al., 1991, J Pharmacol Exp Ther 259(2): 719-24; Green et al., 1971, Am J Ophthalmol 72(5): 897-905). The most commonly used penetration enhancer is benzalkonium chloride (Tang et al., 1994, J Pharm Sci 83(1): 85-90; Burstein et al., 1980, Invest Ophthalmol Vis Sci 19(3): 308-13), which also works as preservative against microbial contamination. It is typically added to a final concentration of 0.01-0.05%.

Particularly, the pharmaceutical formulations of the present invention are intended for topical administration, i.e. topical formulation. The topical formulations may be in the form of ophthalmic solution, ointment, cream, gel, emulsion or dispersion. The topical formulations comprise any one or a combination of the above described solid state forms of Reproxalap in an effective amount for the desired treatment.

The crystalline polymorphs of Reproxalap salts; and the pharmaceutical compositions of Reproxalap salts of the present disclosure can be used as medicaments, particularly in the treatment of dry eye disease, allergic conjunctivitis, noninfectious anterior uveitis, and/or Sjögren-Larsson Syndrome.

The present disclosure also provides methods of treating dry eye disease, allergic conjunctivitis, noninfectious anterior uveitis, and/or Sjögren-Larsson Syndrome comprising administering a therapeutically effective amount of any one or a combination of the crystalline polymorphs of Reproxalap salts of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Analytical Methods

Powder X-Ray Diffraction (XRPD) Method

X-ray diffraction was performed on X-Ray powder diffractometer:

X'Pert PRO PANalytical; CuKα radiation ($\lambda$=1.5418 Å); PIXcel detector; laboratory temperature 22-25° C.; The samples were gently ground by means of mortar and pestle in order to obtain a fine powder.

Measurement Parameters:
  Scan range (°): 3.000-40.001
  Step size (°): 0.0131
  Time per Step (s): 66.3
  No. of steps: 2818
  Scan mode: Continuous
  Sample spinning (Rotation time (s): Spin (1 sec)
  Sample holder: PW1811/16 ring holder with zero background plate Procedure for TGA Analysis:

Thermogravimetric analysis was conducted on a Shimadzu instrument DTA-60A thermogravimetric analyzer. About 5-10 mg sample was placed into a tarred TGA crucible and placed into a TGA furnace. The furnace was heated under nitrogen at a heating rate of 10° C./min up to 300° C.

EXAMPLES

Preparation of Starting Materials

Reproxalap can be prepared according to methods known from the literature (for example U.S. Patent Application Publication No. 2013/0190500).

Example 1—Preparation of Reproxalap Borate Form R1

Reproxalap (0.2 grams) was dissolved in 1 ml of methanol at 20-30° C. in 5 ml vial and stirred for 10 minutes to obtain a clear solution. To the clear solution added boric acid (1.0 eq) under stirring then the clear solution was heated to 50° C. in 15 minutes and maintained for 15 minutes, then it was cooled down to temperature of about 20-30° C. over a period of 60 minutes and the obtained slurry was maintained for overnight at same temperature then further cooled to 5° C. over a period of 30 minutes and maintained for 2 hours at same temperature. The obtained solid was filtered under vacuum at temperature of 20-30° C. and was suck dried for 15 minutes at same temperature and further dried in Vacuum Tray Dryer at 60° C. for 8 hours to obtain Reproxalap borate salt. The obtained solid was analyzed by XRPD, Reproxalap borate Form R1 was obtained, XRPD pattern is shown in FIG. 1.

Example 2—Preparation of Reproxalap 1,5-Naphthalenedisulfonate Form S1

Reproxalap (0.2 grams) was dissolved in 2 ml of methanol at temperature of about 20-30° C. in 5 ml vial and stirred for 10 minutes to obtain a clear solution. To the clear solution added 1, 5-naphthalenedisulfonic acid (1.0 eq) under stirring, after addition of acid, the clear solution transformed to slurry mass then the mass was heated to 50° C. over a period of 10-15 minutes and maintained for 10-15 minutes, then cooled down to temperature of about 20-30° C. over a period 60 min and maintained for 24 hours. The obtained solid was filtered under vacuum at 20-30° C. and suck dried for 15 minutes at same temperature and further dried in Vacuum Tray Dryer at 60° C. for 8 hours to obtain Reproxalap 1,5-naphthalenedisulfonate salt. The obtained solid was analyzed by XRPD, Reproxalap 1,5-naphthalenedisulfonate Form S1 was obtained, XRPD pattern is shown in FIG. 2.

Example 3—Preparation of Reproxalap 1,2-Ethanedisulfonate Form U1

Reproxalap (0.2 grams) was dissolved in 2 ml of methanol at temperature of about 20-30° C. in 5 ml vial and stirred for 10-15 minutes to obtain a clear solution. To the clear solution added 1, 2-ethanedisulfonic acid (1.0 eq) under stirring and the reaction mass was heated to 50° C. in 10-15 minutes and maintained for 10-15 minutes, then cooled down to temperature of about 20-30° C. over a period of about 60 minutes and maintained for 24 hours. To the clear solution added 8 ml of THF and stirred for 2-3 hours at temperature of about 20-30° C. then further cooled to temperature of about 5° C. over a period of about 30 minutes and maintained for 3 hours at same temperature. The obtained solid was filtered under vacuum and suck dried for 15 minutes and further dried in Vacuum Tray Dryer at 60° C. for 8 hours to obtain Reproxalap 1,2-ethanedisulfonate. The obtained solid was analyzed by XRPD, Reproxalap 1,2-ethanedisulfonate Form U1 was obtained, XRPD pattern is shown in FIG. 3.

Example 4—Preparation of Reproxalap Methanesulfonate Form P1

Reproxalap (0.2 grams) was dissolved in 2 ml of ethanol at 20-30° C. in 5 ml vial and stirred for 5 to 10 minutes at 20-30° C. to obtain the clear solution. The clear solution was heated to 50° C. and stirred for 5 minutes. To the clear solution added methane sulfonic acid (1.0 eq) in 0.84 ml of THF and maintained for 10-15 minutes at same temperature, then it was cooled down to temperature of 5° C. over a period of 9 hours and maintained for 11 hours at same temperature, then the temperature was raised to about 20-30° C. over a period of 10 minutes. 2 ml of MTBE was added at 20-30° C. and maintained for 4-5 hours at same temperature and the reaction mass was continuously stirred overnight at same temperature, added 12 ml of MTBE in the reaction mass, sticky mass observed in 10-15 minutes, stirring was continued at same temperature. The solid was observed after 30-45 minutes and maintained for 1 hour at same temperature. The obtained solid was filtered under vacuum at temperature of 20-30° C., washed with 1-5 volume of MTBE, and suck dried for 10-15 minutes at same temperature to obtained Reproxalap methanesulfonate salt. The obtained solid was analyzed by XRPD, Reproxalap methanesulfonate Form P1 was obtained, XRPD pattern is shown in FIG. 4.

Example 5—Preparation of Reproxalap Methanesulfonate Form P1

Reproxalap (1 gram) was dissolved in 10 mL of ethanol at temperature of about 20° C. to 30° C. in 5 mL vial and stirred for a period of about 5 minutes to 10 minutes at temperature of about 20° C. to 30° C. to obtain the clear solution. The clear solution was heated to 50° C. and stirred for 5 minutes. Methane sulfonic acid (1.0 eq) in 4.2 mL of THF was added to the clear solution and was maintained for a period of about 10 minutes to 15 minutes at same temperature, then it was cooled to temperature of about 5° C. to 20° C. over a period of about 30 minutes. 70 mL of MTBE was added at temperature of about 5° C. to 20° C. and slurry was formed and maintained for 2 hours at same temperature. The obtained solid was filtered under vacuum at temperature of about 20° C. to 30° C., washed with 1 volume to 5 volume of MTBE, and suck dried for period of about 10 minutes to 15 minutes at same temperature, dried at temperature of about 30° C. to 40° C. in vacuum dryer for a period of about 12 hours to 15 hours to obtain Reproxalap methane sulfonate salt.

The invention claimed is:

1. Crystalline Form P1 of Reproxalap Methanesulfonate, characterized by data selected from one or more of the following:
   a. an XRPD pattern having peaks at 8.2, 13.4, 17.7, 18.1, 20.6 and 25.9 degrees 2-theta±0.2 degrees 2-theta;
   b. an XRPD pattern as depicted in FIG. 4; and
   c. combinations of these data.

2. Crystalline Form P1 of Reproxalap Methanesulfonate according to claim 1, characterized by an XRPD pattern having peaks at 8.2, 13.4, 17.7, 18.1, 20.6 and 25.9 degrees 2-theta±0.2 degrees 2-theta, and also having one, two, three, four or five additional peaks selected from 11.0, 15.3, 22.5, 23.2 and 29.3 degrees two theta±0.2 degrees two theta; or characterized by an XRPD pattern having peaks at: 8.2, 11.0, 13.4, 15.3, 17.7, 18.1, 20.6, 22.5, 23.2, 25.9, 29.3 degrees 2-theta±0.2 degrees 2-theta.

3. Crystalline Form P1 of Reproxalap Methanesulfonate crystalline Form R1 according to claim 1, wherein the crystalline form is a hydrate form.

4. Crystalline Form P1 of Reproxalap Methanesulfonate according to claim 1, which is polymorphically pure, or wherein the solid state form contains about 20% or less of any other solid state forms of Reproxalap Methanesulfonate.

5. A pharmaceutical composition comprising Crystalline Form P1 of Reproxalap Methanesulfonate according to claim 1.

6. A pharmaceutical formulation comprising Crystalline Form P1 of Reproxalap Methanesulfonate according to claim 1, and at least one pharmaceutically acceptable excipient, wherein the pharmaceutical formulation is an ophthalmic solution, a topical cream, or an ointment.

7. A process for preparing a pharmaceutical formulation according to claim 6, comprising combining the Crystalline Form P1 of Reproxalap Methanesulfonate with at least one pharmaceutically acceptable excipient.

8. A medicament comprising the Crystalline Form P1 of Reproxalap Methanesulfonate according to claim 1.

9. A method of treatment of dry eye disease, allergic conjunctivitis, noninfectious anterior uveitis or Sjögren-Larsson Syndrome comprising administering a therapeutically effective amount of the Crystalline Form P1 of Reproxalap Methanesulfonate according to claim 1, to a subject in need of the treatment.

10. A method of treatment of Sjögren-Larsson Syndrome comprising administering a therapeutically effective amount of the Crystalline Form P1 of Reproxalap Methanesulfonate according to claim 1 to a subject in need of the treatment.

11. A process for preparing a Reproxalap salt or a solid state form thereof or Reproxalap base or a solid state form thereof, comprising preparing the crystalline Form P1 of Reproxalap Methanesulfonate according to Claim 1, and converting it to another Reproxalap salt or a solid state form thereof, or Reproxalap base or a solid state form thereof.

* * * * *